United States Patent [19]

Terminiello et al.

[11] Patent Number: 4,774,192
[45] Date of Patent: Sep. 27, 1988

[54] A DRY REAGENT DELIVERY-SYSTEM WITH MEMBRANE HAVING POROSITY GRADIENT

[75] Inventors: Louis Terminiello, Sunrise; Jack L. Aronowitz, Delray Beach, both of Fla.

[73] Assignee: Technimed Corporation, Ft. Lauderdale, Fla.

[21] Appl. No.: 7,983

[22] Filed: Jan. 28, 1987

[51] Int. Cl.⁴ ............... G01N 33/52; G01N 33/53; G01N 33/62; G01N 33/66
[52] U.S. Cl. ............... 436/530; 422/56; 435/11; 435/12; 435/14; 435/22; 435/25; 435/805; 435/810; 436/518; 436/531; 436/808; 436/810; 436/817; 436/901
[58] Field of Search ............... 422/56; 435/4, 7, 11, 435/12, 14, 805, 810, 22, 25; 436/810, 518, 531, 530, 808, 817, 901

[56] References Cited

U.S. PATENT DOCUMENTS

| | | | |
|---|---|---|---|
| 3,630,957 | 12/1971 | Rey | 435/805 X |
| 3,975,162 | 8/1976 | Renn | 422/56 X |
| 4,176,008 | 11/1979 | Figueras | 435/12 |
| 4,219,334 | 8/1980 | Schluter | 422/56 X |
| 4,543,338 | 9/1985 | Chen | 435/14 X |
| 4,594,224 | 6/1986 | Okaniwa | 435/805 X |
| 4,594,327 | 6/1986 | Zuk | 435/805 X |
| 4,621,049 | 11/1986 | Wang | 435/805 X |
| 4,632,901 | 12/1986 | Valkirs | 435/805 X |
| 4,637,978 | 1/1987 | Dappen | 435/805 X |

Primary Examiner—Sidney Marantz
Attorney, Agent, or Firm—John H. Faro

[57] ABSTRACT

Dry chemistry reagent system, kit and method for detection of an analyte such as glucose, cholesterol, urea, antigen or antibody. The reagent system is a porous membrane or bibulous film having a porosity gradient from one planar surface to the other. In the membrane are uniformly distributed an indicator, a flow control agent and a reagent cocktail. The membrane is also modified by a conditioning agent.

40 Claims, 2 Drawing Sheets

A DRY REAGENT DELIVERY SYSTEM WITH MEMBRANE HAVING POROSITY GRADIENT

BACKGROUND OF THE INVENTION

1. Field of the Invention

This invention is directed to articles of manufacture and to analytical methods. More specifically, this invention resides in the provision of a highly effective delivery system for dry chemistry reagents; and, in the incorporation of this delivery system into a plurality of diverse test strips. It is understood that the phrase "dry chemistry reagents" is inclusive of reagent systems for both clinical chemistry assays and immunoassays. This dry chemistry reagent system is useful in the rapid and efficient analysis of biological fluids. One of the unique features of this system is its ability to accomplish such analysis of samples containing cellular and particulate matter or macromolecules without prior seperation of such endogenous materials from the sample. Such separation is generally desirable, and can be essential in certain analysis to prevent such materials from masking detection of a reporter molecule which is indicative of the presence of the analyte of interest.

2. Description of the Prior Art

The search for a simple and effective means for performance of analytical testing of heterogenous fluid samples, notably biological samples, has spanned more than twentyfive years. Much of the early work in this area was directed to the development of a reagent format which would be compatible with a simple yet effective analytical protocol. Probably one of the simpler of these systems was based upon the provision of a "dry reagent chemistry system"; that is, a reagent system that was imbibed into an absorbent medium, dried and reconstituted by simple addition/absorption of the fluid sample by the absorbent medium.

The patent and technical literature is voluminous regarding the development and refinement of such dry chemistry reagent systems. These systems have traditionally included the reagent coated tube technology, the reagent coated bead technology and the so-called "paper" or "bibulous" layered systems. A format of dry chemistry reagent system which continues to enjoy increasing popularity is based upon single and multi-layered bibulous media.

One of the earlier and more successful of adaptations of the bibulous media format for dry chemistry reagent systems involved the development of a series of assays for analysis of whole blood. Some of the earlier patents in this field described the adaptation of this format to analysis of heterogenous fluids (whole blood) for glucose and other common analytes (i.e. urea, cholesterol) of interest. The following list is representative of the patent literature directed to simple analytical devices (test strips) illustrating the adaptations of dry chemistry reagent system to analysis of heterogeneous biological fluids: U.S. Pat. Nos. 3,061,523 (to Free); 3,552,925 (to Fetter); 3,607,093 (to Stone); 3,092,465 (to Adams); 3,298,789 (to Mast); and 3,630,957 (to Rey).

U.S. Pat. No. 3,061,523 (to Free), describes the basic chemistry reagent system which has become the standard for colorimetric determination of glucose in biological samples. The chemistry system described by Free is contemplated for use in conjunction with a "dip stick" test. In a typical configuration of the Free invention, a solid phase (i.e. sticks or test strips) is pre-treated with his novel chemistry formulation. The reagent treated portion of this solid phase can thereafter be contacted with a sample suspected of containing glucose. The intensity of color which is developed as a result of such contact is compared to a control or standard and a semi-quantitative determination of glucose level in the sample thereby computed.

In the specific embodiments of the Free device, the dry chemistry reagent system is prepared by first dissolving the reactive constituents in a gelatin base and thereafter impregnating strips of filter paper with this dry chemistry reagent system. This is achieved by simply immersing the filter paper in the gelatin base/reagent system for a sufficient interval to effect impregnation of the reagents into the filter paper. The filter paper treated in this fashion is thereafter dried. The gelatin component of the impregnating solution is reportedly essential to the uniformity of color development. Presumably, the presence of the gelatin controls or inhibits the migration of fluids within the filter paper, thereby minimizing chromatographic separation of reagents and/or sample.

A drop of blood (preferably whole blood) is then applied to the portion of the filter paper containing the dry chemistry reagent system; allowed to react with the reagents contained therein (for approximately 60 seconds) and, thereafter the blood (presumably the red cells) rinsed from the paper. The intensity of the color indicator which is developed as a result of the interaction of the glucose and the reagents within the paper, is thereafter observed or measured. The recommendation (if not a requirement), of the Free system, that the red cells be rinsed from the surface of the test strip, implies that their removal is desirable, if not essential, to observation/measurement of the colored indicator. The rinsing of the red cells from the test strip can be expected to introduce analytical error into such analysis, thus, impairing the accuracy of the test results.

Where the technician performing this test is dealing with a patient sample that may contain infectious microorganisms or viruses, the requirement that the sample be rinsed of red blood cells unnecessarily exposes the technician to potential infection.

U.S. Pat. No. 3,552,925 (to Fetter), represents an improvement to the glucose test element described in the Free patent. Fetter discloses a method and device for effectively separating the whole blood sample into its serum components and into its erythrocyte components (red blood cells and other color forming constituents). Fetter achieves this separation by treatment of a defined area of his sample collection device on his test element with certain water soluble salts. The contact of the whole blood sample with these salts in the test element results in the localized reaction of the erythrocytes (and the other colored components of the whole blood) with these salts and the resultant separation of the serum component therefrom. The serum fraction is, thus, free to migrate or diffuse into the test element. The migration and/or diffusion of the serum component is generally via capillary action or some other passive transport mechanism. The manner in which the sample is applied and the nature of the test medium, effectively transports and distributes the serum to another defined chemically reactive area of the test element containing test reagents. The test reagents of the test element are specific for one or more analytes of interest in the serum fraction (i.e. glucose, galactose, urea, uric acid, phenylalinine and/or various enzymes).

The various configurations of the Fetter test element contemplate a single laminae (FIGS. 1 and 8), having discrete areas of chemical treatments; or a multi-layered structure, wherein a single chemical treatment is confined to each of the layers of the laminate (FIGS. 3 through 7).

Fetter also indicates that the same matrix can be used to retain both the separating reagent and the reagent specific for the analyte of interest. In this latter embodiment of his invention, the whole blood sample would be applied to one side of the strip held in the horizontal position. After adequate penetration of the sample into the matrix containing both the separating and test reagents, the test strip would be inverted and color development observed (if any) on the site opposite the site of application of the whole blood sample.

Fetter is not apparently concerned with potential interference of the colored blood components with the development and/or observation of the indicator species. It is, however, apparent that at low concentrations of analyte, the highly colored blood components could interfere and/or mask the presence of the indicator from visual observation/detection.

Canadian Pat. No. 659,059 represents one of the earlier attempts at preparation of unitary dry chemistry reagent system in a single layer format. The dry chemistry reagent system of this patent is based upon the preparation of a common slurry containing the reactive components of the system along with the ingredients of the bibulous medium (i.e. cellulose acetate). The resultant slurry is then cast and dried. The reactive components of the system are physically entrapped within the resultant film/coating. The physical nature of the film/coating lends itself to absorption of a fluid sample without release (leaching) of the reactive components.

U.S. Pat. No. 3,092,465 (to Adams) describes a diagnostic device for detection of glucose in a heterogenous biological fluid sample (i.e. blood or urine). The device consists of a bibulous medium containing a dry chemistry reagent system specific for reaction with a glucose; and, the manifestation of such reaction by production of a visible change in color. This bibulous medium is provided with a "protective coating" in the form of a semipermeable membrane. This membrane is selective for the exclusion of larger molecules (i.e. proteins and hemoglobins) while freely allowing the fluid fraction containing the glucose to be absorbed by the bibulous medium. This protective coating thus allows the test strip supporting the dry chemistry reagent system to be dipped or immersed in the test fluid without absorption of the colored components of the sample. The protective coating of the sample receptive surface can then be wiped free of an interfering particulate or colored matter prior to monitoring for color change. The wiping of the surface of the analytical element can introduce analytical error into such analysis, thus, impairing the accuracy of the test results. Similar error is to be expected if such debris were removed by washing or other physical means.

U.S. Pat. No. 3,298,789 (to Mast) describes a test article for detection of glucose in heterogenous fluid samples (i.e. whole blood). This test article is composed of a layer of bibulous material impregnated with a dry chemistry reagent system. This layer is overcoated with a smooth semi-permeable film of transparent ethyl cellulose. The test device is used to detect glucose in whole blood by simply applying a whole blood sample (2-3 drops) on the surface of the semi-permeable film coating which has been applied to the reagent impregnated material. After a brief interval, the fluid fraction of the sample is absorbed by the bibulous material. The cellular (colored) fraction of the sample is then wiped off the surface of the semi-permeable film to allow for observation/measurement of the indicator produced by reaction of the glucose and reagents within the bibulous layer. The surface characteristics of this semi-permeable film are thus critical to the operation of this device in the analytical environment. More specifically, the degree of smoothness of the protective film (surface porosity) is critical and must be sufficiently fine to avoid penetration of the cellular components and hemoglobin fractions into the surface of the film. As noted in the discussion of the Free and Adams patents, the removal of cells and colored debris from the sample receptive surface of the test element can introduce analytical error into such analysis.

U.S. Pat. No. 3,607,093 (to Stone) describes a liquid permeable membrane, of uniform chemical composition, having within its matrix, a dry chemistry reagent system. The membrane selected by Stone for his device is similar in its surface characteristics to the protective film of Mast. The analytical protocol utilizing the Stone device is also similar to that of Mast and requires the physical wiping of the sample receptive surface of the membrane for removal of cellular debris and colored materials (from the sample) to allow for observation/measurement of a reaction product indicative of the presence of the analytes of interest. The Stone analytical system suffers from the same deficiency which is common to Free, Mast and Adams, previously discussed; namely, the introduction of analytical error by required physical removal or washing of the cellular and colored debris from the sample receptive surface of the analytical element, prior to monitoring for indicator development.

Additional modification and enhancements have been made to the basic dry reagent chemistry formats described above. These modifications and enhancements have focused upon providing multiple test zones on a common test element; increasing the precision and correlation of indicator development with concentrations of analyte; and, greater control in absorption/distributions of the sample within the bibulous reagent impregnated medium. The following patents are illustrative of the enhancements and modification the dry reagent chemistry format: U.S. Pat. Nos. 3,847,822 (to Shuey); 3,802,842 (to Lange); 3,964,871 (to Hochstrasser); and 4,160,008 (to Fenochetti).

U.S. Pat. No. 3,802,842 (to Lange et al) describes a test strip incorporating a dry chemistry reagent system in which a sample receptive surface of an indicator (reagent) layer is covered by a fine mesh. The indicator layer can be supported upon a "colorless" and "transparent" support. The addition of the fine mesh to this test element reportedly results in enhancement in speed and uniformity of distribution of sample upon the surface of the indicator layer. This uniformity of distribution also reportedly results in substantial improvement in reproducibility of result.

U.S. Pat. No. 3,847,822 (to Shuey) describes what he terms an "asymmetric" membrane comprising a polymer blend of polyvinyl pyrolidone and cellulose acetate. The composition of the membrane reportedly has improved transport of blood solutes; notably insulin, while being substantially impermeable to albumin.

U.S. Pat. No. 3,964,871 (to Hochstrasser) describes a disposable indicator (test strip) having a built-in color intensity scale which is directly correlated to analyte concentration with a test sample. Accordingly, it is reportedly possible to simply immerse this indicator within a test sample and observe the progressive development in color within the various regions of the device. The development of color (indicator) within a specific region of the test strip can thus be directly correlated with a specific concentration of analyte.

U.S. Pat. No. 4,160,008 (to Fenochetti) describes a test device for performance of a clinical analysis of a sample for different analytes on a common support. The inventor has effectively isolated each distinct analytical test in separate zones on the common support by elevating the reagent specific layer above the common support and providing a blotter on the support to insure against run-off and cross-contamination of one analytical site by another.

The next generation (at least in terms of complexity) of dry chemistry reagent systems which has evolved is a multiple layered element, having at least three discrete functional layers. These discrete functional layers are a spreading layer, a reagent layer and a signal (indicator) layer.

The performance of glucose determinations on whole blood, utilizing multiple layered films, is the subject of numerous publications and issued patents. The following listing is representative of the technical publications in this area: Walter, B., Dry Reagent Chemistries in Clinical Analysis, Analytical Chemistry, Vol. 55, No. 4, pp. 498–514 (April, 1983); Curme, Henry G., et al., Multilayer Film Elements for Clncal Analysis: General Concepts, Clinical Chemistry, Vol. 24, No. 8, pp. 1335–1342 (August, 1978); Spayd, Richard W., et al., Multilayer Film Elements for Clinical Analysis: Applications to Representative Chemical Determinations, Clinical Chemistry, Vol. 24, No. 8, pp. 1343–1350 (August, 1978); Ohkubo, Akiyuki, et al., Plasma Glucose Concentrations of Whole Blood, as Determined with a Multilayer-Film Analytical Element, Clinical Chemistry, Vol. 27, No. 7, pp. 1287–1290 (July, 1981); Ohkubo, Akiyuki, et al., Multilayer-Film Analysis for Urea Nitrogen in Blood, Serum, or Plasma, Clinical Chemistry, Vol. 30, No. 7, pp. 1222–1225 (July, 1984); and, Rupchock, Patricia, et al., Dry-Reagent Strips Used for Determination of Theophylline in Serum, Clinical Chemistry, Vol. 31, No. 5, pp. 737–740 (May, 1985). The following listing is representative of the corresponding patent literature in this area: 4,042,335 (to Clement); 4,059,405 (to Sodickson, et al); 4,144,306 (to Figueras); 4,258,001 (to Pierce); and, 4,366,241 (to Tom, et al).

U.S. Pat. No. 4,042,335 (to Clement), describes a series of multilayered analytical element suitable for performing chemical analysis of whole blood samples. The Clement configurations all contemplate the application of test samples either directly, or from a spreading layer, onto a reagent layer. The reagent layer contains a complement of chemicals for reaction with a specific analyte suspected of being present in the test sample. If the analyte is present, a "detectable species" is formed or released from the reagent layer and diffuses into what is termed a "registration layer"—that is, a layer whose sole function is to provide a medium or repository from which the detectable species can be observed or measured. In order to avoid interference (masking) in the observation or measurement of the detectable species, the registration layer is both devoid of the test sample and reagents used in the generation of the diffusible species. In the preferred embodiments of the Clement test element, an optical screen ("radiation blocking layer") is also provided between the reagent layer and the registration layer. This optical screen effectively optically isolates the detectable species from other constituents which could interfere in its detection and/or measurement.

As is evident from the foregoing description, Clement attempts to segregate the individual functions of his analytical element into discrete layers. This technique, although potentially attractive to a manufacturer in possession of technology for fabrication of multilayered elements, is by its very nature unduly complex and potentially troublesome due to the mechanical instability of these composites. More specifically, where this test element is to be used by an individual in a self-test environment, the composite must necessarily be supported on an additional element to lend physical integrity to the multi-layered element and thereby prevent its unintended flexing and potential separation of the various layers contained therein.

U.S. Pat. No. 4,059,405 (to Sodickson, et al), describes a method and apparatus for glucose analysis of whole blood samples. In the Sodickson system (as described in Example 1 d.), a reaction site is initially prepared by preforming wells in a polyox resin treated filter paper. A reaction site is physically defined in this treated paper by impressing thereon a confining ring approximately one centimeter in diameter. A glucose reagent is then applied to the reaction site defined by this ring and the reaction site dried. An ultrafiltration membrane is placed over the well and a sheet of paper containing a dried blood spot placed in contiguous relationship with the ultrafiltration membrane. The dried blood spot is then reconstituted by the addition of saline. The apparatus used in the Sodickson system (i.e. press) confines the reconstituted blood sample in the reaction well for a brief incubation period. During this incubation period, soluble components of the whole blood sample are redissolved in the saline and pass through the ultrafiltration membrane where they come in contact with the glucose test reagents in the polyox treated paper. The cellular components of the blood are retained on the ultrafiltration membrane and thereby prevented from interference with the development and/or measurement of the glucose manifesting indicator.

The system described by Sodickson, as contemplated in his Example 1 d., is cumbersome (requiring reconstitution of the blood sample and relatively complex equipment to effect separation of cellular components from the whole blood sample) and does not readily lend itself to self-testing.

U.S. Pat. No. 4,144,306 (to Figueras), describes a multi-layered analytical element analogous to that of the Clement patent (previously discussed). The Figueras chemistry differs from Clement in that the interaction of an analyte and non-diffusible reagents in the reagent layer, results in the release of a "preformed detectable species" which can migrate from the reagent layer into a registration layer. This preformed detectable species is then observed or measured in the registration layer. Figueras contemplates (as described in his Example VI) the adaptation of his system to glucose analysis of whole blood. The separation of colored and cellular components of the whole blood would be achieved by Figueras in essentially the same fashion as in the Clement patent. The introduction of the whole blood sample into the reagent layer of the Figueras element results in the release of a diffusible preformed photographic dye, which is then free to migrate into the registration layer. Figueras requires the presence of the same type of optical screen (radiation blocking layer) between the reagent layer and the registration layer to avoid masking or interference in detection of the dye form the non-diffusible color components (i.e. sample and reagents) in the reagent layer. The limitations and disadvantages noted in the discussion of the Clement patent are also applicable to the multi-layered analytical element of Figueras. Figueras, however, introduces an additional complexity; namely, the effective immobilization of the reagents within the reagent layer and the preservation of the preformed indicator prior to its release by the analyte of interest. Because of the requirements of maintenance of fluid contact between the various elements of the Figueras composite, its mechanical properties are critical. Accordingly, the multi-layered element of Figueras, as previously noted for Clement, will require a supporting (transparent) layer to lend physical integrity to this device.

U.S. Pat. No. 4,258,001 (to Pierce et al), describes a multi-layered analytical element (of the type described in both Clement and Figueras—previously discussed) incorporating a unique spreading layer. The spreading layer of the Pierce patent is described as an essentially "non-fibrous" material. In one of the preferred embodiments described by Pierce (Figure III), the spreading layer can contain "interactive compositions" (test reagents) for reaction with analytes in a test sample. Pierce also contemplates the use of her device in the analysis of whole blood, blood serum and urine. Whole blood can be applied directly to the Pierce element. The presence of red blood cells will not reportedly interfere with spectrophotometric analysis if carried out by reflectance measurements, provided a radiation screen (blocking layer) is used to screen out interference from the red cells (column 26, line 49–61).

As is evident from the above patent, the Pierce device is designed to "take up" the whole blood sample. Thus, both cellular and non-cellular components of the whole blood are imbibed by the spreading layer. The spreading layer of Pierce is, therefore, not intended nor contemplated as a means for separation of the cellular fraction of the blood from the serum fraction. Where enzyme based diagnostic clinical assays are incorporated into the spreading layer (as in the case of glucose analysis), the potential for inhibition of these enzymes by the erythrocytes can potentially mask low concentrations of glucose and, thus, distort an otherwise clinically significant result.

The transport and spreading of biological samples is of concern, not only in dry chemistry reagent systems for performance of clinical assay, but also in the dry reagent systems utilized for immunoassay of the same biological fluids. The following U.S. Patents are representative of the immunoassay literature in this area: U.S. Pat. Nos. 4,094,647 (to Deutsch); and, 4,366,214 (to Tom et al).

U.S. Pat. No. 4,094,647 (to Deutsch), describes a linear wick having defined areas for placement of reagents and sample. The end of the wick is placed in a vertical position in a developer fluid and the fluid drawn up the wick by capillary action. As the fluid is drawn into the wick, it transports the reagents and sample, from their respective locations, into contact with one another. One or more of these reagents can be immobilized on the wick; thus, the developer fluid is used to transport reagent and sample to the immobilized reagent and any unreacted or mobile materials from the immobilized reagent. The site having the immobilized reagent can then be viewed or measured for the presence of analyte.

U.S. Pat. No. 4,366,241 (to Tom et al) describes a device for the nonchromatographic immunoassay of biological fluids. In the Tom device configuration, a test element, having a relatively small test zone, is treated with an immobilized binding material (termed "mip" or "member of an immunological binding pair"). The test zone of this device is the exclusive entry port for the biological sample and is designed for receipt of the biological sample either by direct application or immersion in the test fluid. The analyte (if any) contained in the biological sample is selectively (immunochemically) bound in the test zone to the immobilized binding material which is specific for this analyte. The residual components of the sample, including the fluid component thereof, are drawn from the test zone to a second element which is in fluid contact (contiguous relationship) with the test zone. The second element's function is to pump or draw the biological sample through the test zone into the test element. Those constituents of the sample which are not bound in the test zone are, thus, drawn into the test element and away from the test zone.

In the immunological test element of the type described by Tom, the pretreatment of the test zone effectively confines the analyte and the test reagents (i.e. labelled indicator) to the analysis site, thereby essentially eliminating the problems of reagent and sample migration (which are common in the solid phase systems designed for clinical chemistry analysis). These immunoassay systems of Tom are not, however, without their disadvantages, the most common being the nonspecific binding of interfering substances in the reaction zone and the difficulties which are sometimes inherent in the detection of low levels of analyte.

U.S. Pat. No. 4,446,232 (to Liotta) describes a multiple layer test device for immunoassay. This device and test protocol are directly analogous to the Figueras patent (previously discussed). The addition of sample containing an analyte of interest results in the displacement of a previously immobile species. In the system described by Liotta, the component of the reagent system which is displaced is an enzyme conjugated to a member of an immunological binding pair (hereinafter "conjugate"). The conjugate is then carried into the laminate where it can effect production of a detectable species.

As is evident from the foregoing discussion of the references appropriate for whole blood analysis, each type of test element generally requires a plurality of lamina in its preferred configuration. Where a single layer (component) test device is suggested, none of the references, with one exception (U.S. Pat. No. 3,607,093- to Stone), either acknowledge or appreciate the potential chemical and optical interference of the erythrocyte population (and other colored components of the blood), on the analytical protocol or in the detection of the reaction product which is indicative of the presence of the analyte (namely, the glucose). Where immobilization techniques (as described in Fetter, Deutsch and Tom) are employed, the specificity of the binding reaction can, under certain conditions, be indiscriminate. In the case of Fetter, the attempt at scavenging of erythrocytes and other colored components from the sample with certain salts (that have been imbibed within the test medium), is not without its limitations. In the single layered element of Fetter, the serum fraction is radially separated from the colored component of the blood and thereby results in the distribution of the analyte over a relatively large area. If the analyte is present in low concentrations, it can easily escape detection. Thus, some amplification mechanism may be required for visualization of a low level of analyte (i.e., the use of an enzyme in conjunction with a chromogenic substrate).

The immunochemical device and techniques of the type described by Deutsch, Tom amd Liotta are not readily compatible with whole blood analysis. It is possible to wash the test element for removal of the cellular debris (as is suggested in the Free patent), however, the effect of such additional step upon the immunochemical binding process is not known and can be expected to introduce analytical error in such analysis. Such manipulations of the test element can also be expected to mask detection of the analyte manifesting reaction or removal (in part) of the indicator species which is indicative of the analyte of interest. In addition, such physical removal of cellular and colored debris will necessarily expose the clinician or the person performing the test to potential infection by those components of the blood which are removed from the test element.

In summary, it should now be apparent that the prior art lacks a simple yet accurate device for analysis of whole blood. Where such devices have been proposed, they are complex, do not readily lend themselves to self-testing without the provision of a fixture or additional support mechanism, and generally lack the sensitivity to permit differentiation of different levels of analyte over a broad clinical range of concentration. Moreover, all such devices discussed above (with the exception of the Stone patent) would appear to have one common failing; namely, their inability to effect optical (and in certain instances, chemical) isolation of erythrocyte and other colored components of the whole blood from the observation/measurement site without the physical removal of the erythrocytes from the test element; or, the provision of some optical screen (blocking layer) between the colored components of the sample and the indicator compound which is generated as a result of the clinical assay.

OBJECTS OF THE INVENTION

It is the object of this invention to remedy the above and related deficiencies in the prior art.

More specifically, it is the principal object of this invention to provide a dry reagent delivery system for clinical and immunoassay of biological fluids.

It is another object of this invention to provide a dry reagent delivery system which is effective in the analysis of biological fluids containing cells, particulate matter and macromolecules (hereinafter collectively referred to as "interferents") without pretreatment (i.e. filtering or centrifugation) or dilution of the biological fluid or the chemical removal/neutralization of such interferents.

It is yet another object of this invention to provide a dry reagent delivery system suitable in the rapid and efficient analysis of whole blood for one or more analytes of interest, without prior separation of the serum from the cellular fraction.

It is still yet another object of this invention to provide a dry reagent delivery system suitable in the rapid and efficient analysis of urine for one or more analytes of interest, without prior concentration and/or chemical extraction of the analytes of interest from the urine sample.

It is an additional object of this invention to provide a dry reagent delivery system suitable in the rapid and efficient analysis of saliva for one or more analytes of interest.

It is yet an additional object of this invention to provide a dry reagent delivery system which is both self-contained and does not require any additional instrumentation or extensive training for performance of a diagnostic assay or interpretation of the result.

It is still yet an additional object of this invention to provide a dry reagent delivery system which is stable and retains its potency and activity until placed in use by contact with a biological fluid.

SUMMARY OF THE INVENTION

The above and related objects are accomplished by the provision of a dry reagent delivery system comprising a conditioned membrane containing a complement of reagents which are specific for reactions with one or more analytes of interest. The interaction of the analyte(s) and such reagents is manifest by the release or formation of an indicator molecule which is indicative of the presence or absence of the analyte in the sample. The sample receptive surface of the membrane is relatively dense, thereby being exclusive of cells, particles and/or macromolecules which can potentially interfere with reaction of the analyte and the reagent system and/or mask the detection of a reporter molecule.

The opposing surface of the membrane, by way of contrast, is substantially less dense (more porous), thereby allowing for infusion of the reagent system during manufacture; and, the formation, diffusion and visualization of a reporter molecule, which is indicative of the analyte of interest.

The dry reagent delivery system can be configured as a component of test strips for analysis of whole blood samples, urine or saliva. In each of these configurations, it is contemplated that this sample receptive surface of the membrane shall be the exclusive means of access of the biological fluid to dry reagent system.

BRIEF DESCRIPTION OF THE DRAWINGS

In each of the following figures, the perspective view is oriented to the side of the test strip intended for application of the biological sample.

FIG. 8 is a cross-section of a test strip having a contiguous wicking or spreading layer.

DESCRIPTION OF THE INVENTION INCLUDING PREFERRED EMBODIMENTS

The reagent delivery system of this invention is unique in (a) the provision of a conditioned membrane within which the analysis of the fluid sample is conducted; (b) the manner of distribution of the analyte specific reagents within the membrane; and, (c) in the ability to effectively segregate the various fractions of a heterogenous sample. This segregation is essential to effectively isolate the component of the sample which is to be subjected to analysis from the fraction of the sample which can potentially interfere with the reaction of the analyte and the reagents specific for its detection, or otherwise mask the detection of a reporter molecule, which is indicative of the presence or absence of the analyte of interest. The ability to physically exclude a portion of sample from absorption by the membrane is based upon a combination of factors, including the inherent density of the sample receptive surface of the membrane and the distribution of the constituents of the reagent delivery system within the matrix of the conditioned membrane.

The membrane which is suitable as a repository of the dry chemistry reagent system is, prior to conditioning, anisotropic, in that there exists a density gradient from one planar surface to the other. The density gradient is typically produced as an incident to its manufacturer. More specifically, where the constituents of the membrane have been cast from a slurry, the particles of the slurry tend to settle (prior to and during the evaporation of the casting fluid) upon a supportive surface. Once the casting fluid has evaporated, the membrane forms a self-supporting film and can be separated from this supporting surface. The settling of particles of the slurry tends to creat a more compact (dense) membrane surface contiguous to this supporting surface. The constituents from which the membrane can be prepared include both synthetic and naturally occurring materials, i.e., nylon, cellulose acetate, cellulose acetate - nitrate esters and mixtures thereof.

The membrane's physical characteristics (tensile strength, thickness, etc.) are of course to be consistent with test strip manufacture; that is, it should have sufficient dimensional stability and integrity to permit sequential absorption and drying of the conditioning agent the reagent cocktail and/or indicator without loss of its physical strength. The physical attributes of the membrane should also preferably provide sufficient durability and flexibility to adapt in automated processes for continuous manufacturing of test strips. The physical characteristics of the membrane should, in addition, be otherwise consistent with the absorption and retention of aqueous fluids in the contemplated environment of use.

The membrane must also be relatively chemically inert; that is, essentially unreactive toward both the constituents of the chemistry reagent system and toward the constituents of a sample which is to be reacted with the reagent system within the membrane. It is, however, to be anticipated that certain of the inherent qualities of the membrane surface and/or its matrix may exhibit some affinity for a constituent of the reagent system and/or a constituent of the fluid sample. This natural attraction can, in certain instances, be used to advantage to immobilize a constituent of the reagent cocktail and/or sample on or within a portion of the membrane and thereby effect a type of separation or anisotropic distribution of the constituents of the cocktail/sample. This type of separation, based upon natural binding affinity of the membrane, can be used to advantage in both clinical chemistry assays and in immunoassay.

The membrane's optical properties should also enable effective observation/monitoring of the reaction manifesting indicator species. This requirement would, thus, contemplate that the membrane provide a background of sufficient contrast to permit observation of the indicator species at relatively low concentrations. Where the indicator is a fluorophore, the background fluorescence of the membrane should be minimal or be essentially non-fluorescent at the monitored wavelength of interest.

Where the inherent characteristics of the membrane are not conducive to effective monitoring of an indicator, it may be desirable to introduce a pigment into the dry chemistry reagent system. For example, certain of the membranes which may be potentially suitable for use in this invention can be colored or transparent. The introduction of pigment into the chemistry reagent system provides a suitable background against which to measure the indicator species.

The transparency of the membrane can, however, be used to advantage in both nephelometry and photofluorometric assays in which the presence or absence of analyte in the sample is manifest as a change in turbidity in the fluid phase. The dry chemistry reagent for such turbidimetric reaction systems will typically include a color, transparency or background modifying pigment which is absorbed into the membrane; preferably along with the conditioning reagent.

1. Preparation of Glucose Test Strips In order to better illustrate the unique features noted above, the reagent delivery system will now be described by reference to a test strip which contains reagents specific for the detection of glucose in whole blood.

The standard chemistry reagent system for detection of glucose has been previously described in U.S. Pat. No. 3,061,523, which is hereby incorporated by reference in its entirety. The basic complement of interactive materials which are required in the reagent to produce a colorimetric reaction for detection of glucose are glucose oxidase, peroxidase, o-tolidine dihydrochloride, and buffering salts/acids.

For the purpose of this illustration, the fluid absorbent medium utilized in this reagent system can be any one of a variety of synthetic (preferably cast) membranes having a relatively dense surface (pore size $<0.5$ microns) and a relative less dense surface (pore size $>1.0$ microns).

The order of absorption of the constituents of the dry chemistry reagent system into the membrane is generally dictated by considerations involving chemical compatibly and/or other factors relating to solubility in a common solvent. Since the o-tolidine solution is highly acidic it is incompatible with the enzymes of the reagent system and, thus, each are absorbed into the membrane separately.

Initially, the membrane is conditioned by treatment with a first solution containing protein, glucose, dextrin or dextrans, starch, polyethylene glycol (PEG), polyvinyl pyrolidone (PVP), or an equivalent. The purpose of such conditioning is two-fold: (a) to effectively reduce the void space within the matrix of the membrane and, (b) to assist or promote the absorption of the fluid fraction of the biological sample. In an alternative embodiment of the method for preparation of this reagent system, the conditioning agent can be combined with one or more of the interactive materials of the reagent system and concurrently absorbed into the membrane. Where the conditioning agent is combined with the interactive materials of the reagent composition, its absorption by the membrane will necessarily be preceded by absorption of the indicator molecule.

Where such conditioning of the membrane is effected independent of the interactive materials of the reagent system, the membrane is dried under controlled conditions, and then contacted with a second solution containing the indicator molecule (or the chemical precursor of the indicator molecule). The absorption of the indicator molecule (or its precursor) can be effected from either the less dense or more dense surface of the membrane, with preference being given to the less dense surface.

Following the absorption of the above solution, the membrane is once again dried under controlled conditions to preserve the uniformity of distribution of the non-fugitive constituents of this solution.

The membrane is then contacted with a third solution containing the balance (interactive materials) of the reagent system. The absorption of this solution is preferably effected by simply contacting the less dense surface of the membrane and this solution and allowing the membrane to soak up the solution like a blotter. This third solution also contains what can be functionally described as a "flow control agent". This agent modulates the rate of spreading/distribution of the fluid fraction of this sample throughout the matrix of the membrane. It is, thus, effective in the prevention of the chromatographic separation of the reagents within the membrane matrix upon the addition of the fluid sample. Following addition of this third solution, the membrane is air dried for removal of excess fluid, lyophilized and shielded from light. The foregoing practices are necessary and appropriate for maintenance of uniformity of reagent distribution and protection against photo-degradation of the indicator.

Once the reagent delivery system has been prepared as described above, the resultant membrane can be adapted to any one of several test strip configurations specific for the analysis of whole blood urine or saliva.

Figures 1, 2, 3:
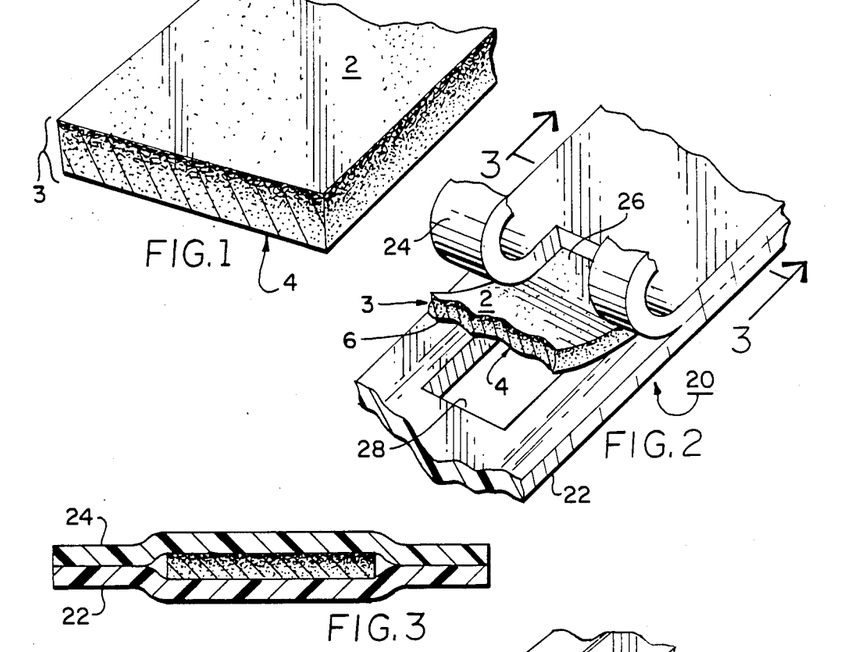
FIG. 1 is a perspective view in partial cross-section through the reagent delivery system of this invention.
FIG. 2 is a perspective view of a test strip for analysis of a whole blood sample incorporating the reagent delivery system of FIG. 1.
FIG. 3 is a cross-sectional view of the test strip of FIG. 2 at section AA.

FIG. 1 is illustrative of the internal structure of the reagent delivery system of this invention. The sample receptive surface (2) of the membrane (3) is essentially impermeable to cells and particulate matter. By way of contrast, the opposing surface (4) is relatively porous. The matrix (6) of the membrane is fairly non-descript, except to note that its inherent void space has been reduced substantially from that originally provided by absorption of the conditioning agent, indicator, interactive reagents and flow control agents. Thus, the relative density of the original membrane has been effectively increased. The density of the membrane containing the dry reagent system is believed to be critical to performance of assay and the uniformity of the membrane. As noted previously, the controlled drying and shielding of the indicator from photodegradation are critical to both effective and consistent performance. The membrane uniformity is also critical to consistent performance of the test strip. The cast membranes have proven to be of more consistent quality and uniformity and are, thus, preferred for the test strip of this invention.

FIG. 2 provides an illustration of the membrane (3) in a test strip (20) intended for analysis of a biological fluid. This test strip configuration is intended for use in protocol contemplating the application of the biological sample to the sample receptive surface (2) of the membrane, allowing for adsorption of the fluid fraction of the sample into the matrix (6) of the membrane and detection of an indicator molecule by inversion of the test, and visually observing indicator development from the more porous surface (4) of the membrane. This test strip can also be inserted into a reflectance meter, nephelometry (measures turbidity), a photometer or fluorometer of the type illustrated in FIG. 9; and, the reporter molecule measured and compared with a standard curve for the analyte of interest. The instrument will then report a value based upon its observation and comparison with a standard.

FIG. 3 provides a cross-sectional view through test strip of FIG. 2 at line 3,3. The membrane (3) is sealed within the components of the test strip by an envelope (22,24) to insure confinement of the test sample upon the sample receptive surface (2) of the membrane. This sealing of the membrane within the envelope simply involves the placement of a piece of water insoluble adhesive (not shown) along the planar surfaces of the envelope which are in contact with the planar surfaces of the membrane. In the configurations illustrated in FIG. 2 and FIG. 4, the sample receptive surface (2) of the membrane (3) is exposed from above and below through a pair of apertures (24,26) in the envelope. The aperture (26) that exposes the sample receptive surface (2) of the membrane defines the lateral dimensions of a well (70) in which the sample is confined. This confinement of the sample (99) is more fully illustrated in FIG. 6.

The second aperture (24) in the envelope exposes the underside (4), or the more porous surface, of the membrane, thereby permitting monitoring of a reaction product which is indicative of the presence or absence of an analog of interest. This ability to observe/measure such reaction product (hereinafter "indicated") without physical removal of the sample residue from the sample receptor surface of the membrane, or optically masking such residue with a separate "blocking layer" (optical screen) is unique to the dry chemistry reagent system of this invention.

Figure 4:
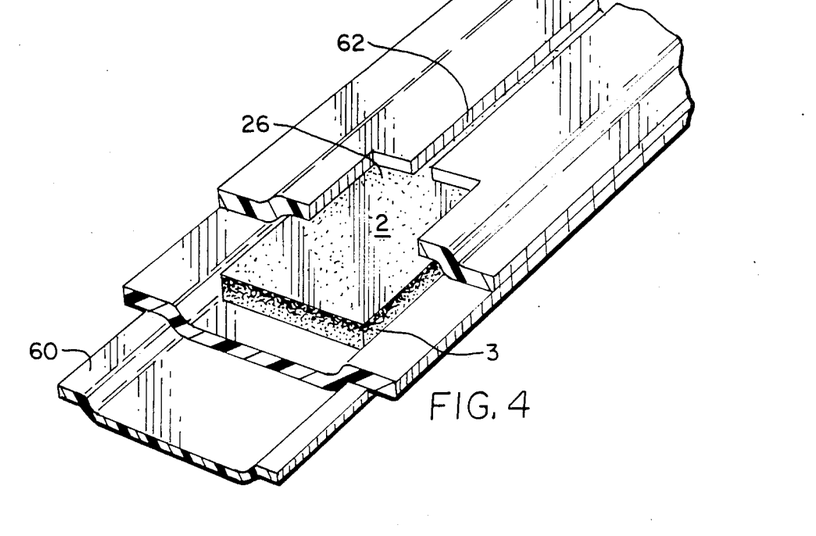
FIG. 4 is a perspective view of a test strip for analysis of a urine sample incorporating the reagent delivery system of FIG. 1.
Figures 5, 6, 7, 8A, 8B, 9:
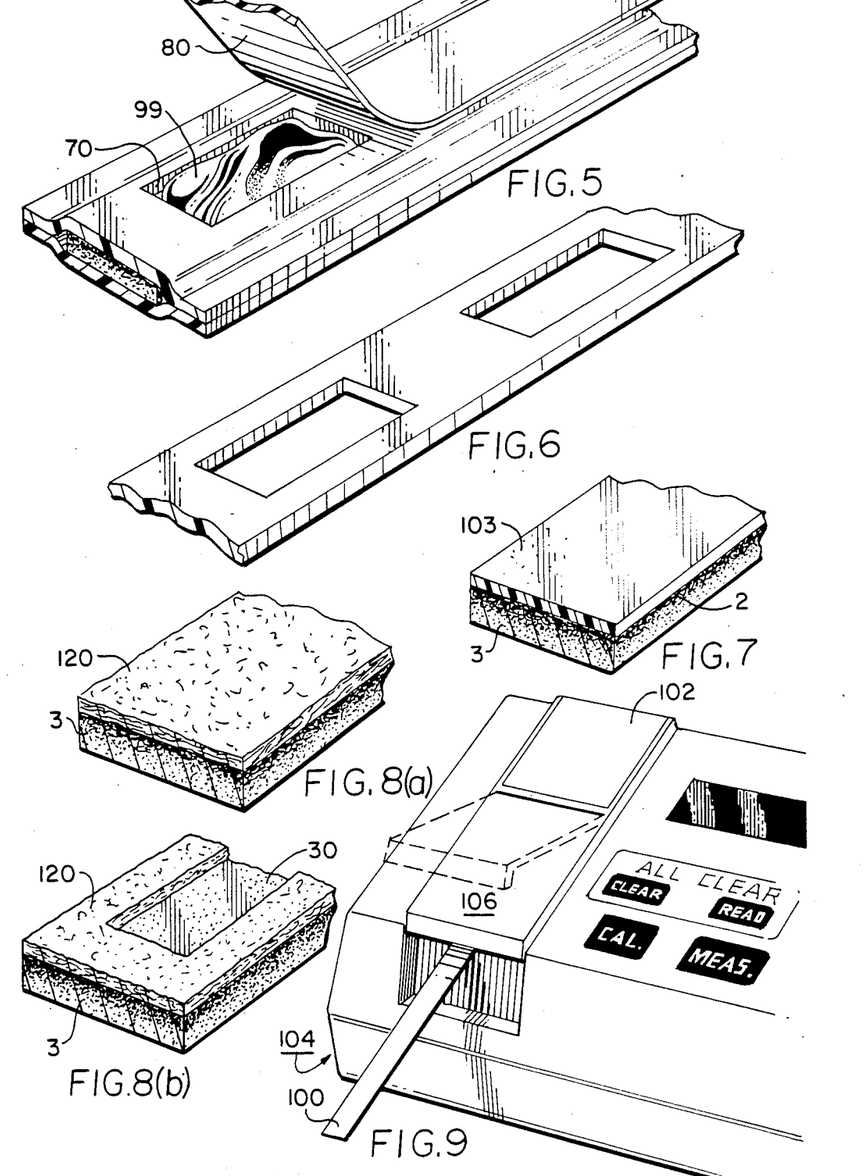
FIG. 5 is an alternative embodiment of the test strip of FIG. 1.
FIG. 6 is an alternative embodiment of the test strip of FIG. 1.
FIG. 7 is a cross-section of a test strip in which a component of the dry chemistry reagent system is coated on the sample receptive surface and the balance of such system within its matrix.
FIG. 9 is a device for monitoring the reaction of analyte with a dry chemistry reagent system of the test strip of FIG. 8.

The test strips illustrated in FIGS. 4 and 5 incorporate the same basic elements of the test strip of FIG. 2 with certain enhancements. More specifically, the test strip of FIG. 4 incorporates a protective film (60) which effectively precludes sample from contact with the underside of the membrane. This test strip is, thus, suitable for immersion in a fluid sample (i.e. dipstick) to effect contact of the sample with the sample receptor surface of the membrane. A slot (62), or air bleed, is provided in the surface of the envelop ( ) to allow for the escape of air trapped in the cavity (not shown) which is formed between the protective film (60) and the underside of the membrane (4).

The test strip illustrated in FIG. 5 incorporates a flap (80) which can be separate from or integral with the test strip. This flap is provided with a pressure sensitive adhesive (not shown) which enables the user to effectively seal the sample (99) within the well (70) defined by the aperture of the envelope and the sample receptor surface of the membrane. This confinement of the sample within the test strip provides significant protection of the clinician from inadvertent contact with an infectious specimen; and, also prevents unintended transfer of sample residue to surfaces of an analytical device (i.e. fluorometer) which can be used to monitor the concentration of an indicator produced within the membrane. With respect to this latter point, the test strip is compatible for use in a variety of environments, including use with a monitor of the type illustrated in FIG. 9.

In practice, a test strip (100) of the configuration of FIG. 5 (having a sample sealed within the speciment well) is inserted into the read station (not shown) of the monitor (104). This is accomplished by simply raising the door (106) located on the top of the monitor housing and positioning the test strip within the read station of the monitor. The test strip is oriented in a manner to align the aperture on the underside of the test strip with the photo optical elements (not shown) of the monitor. The placement and orientation of the test strip generally involves at least some contact of one or more surfaces of the chamber housing and photo optical elements with the test strip. The failure to isolate the sample in the manner illustrated in FIG. 5 will inevitably result in contamination of this chamber and possible damage to the monitor, or introduction of imprecision in the measurement of subsequent samples. After the requisite interval, the monitor has had an opportunity to measure the level of indicator in the test strip. The test strip is then removed from the monitor and discarded.

FIG. 6 is illustrative of an alternative embodiment of an envelope for a test strip of this invention. This envelope has multiple apertures and is designed for containment of separate pieces of membrane containing different dry chemistry reagent systems. Accordingly, a device of this configuration has the potential for performance of a clinical chemistry profile analysis of an individual patient sample on a single test strip.

FIG. 7 is illustrative of an embodiment of the dry chemistry reagent system of this invention in which a component of the reagent system is deposited upon the sample receptive surface of the membrane as a thin film or coating (103). The separation of the constituents of the reagent system form one another in the dry stage is only a temporary condition. Upon application of the fluid sample to this coating, it is anticipated that the analyte of interest will displace a component of the reagent system or somehow react therewith, thus, permitting this component of the reagent system to be freely absorbed into the membrane where it can initiate a discernible reaction which is indicative of the presence or absence of the analyte of interest.

FIG. 8(a) is illustrative of a dry chemistry reagent system having a spreading layer (12) in a contiguous relationship (i.e. fluid contact) with the sample receptive surface (2) of a membrane (3). The spreading layer facilitates the distribution of sample on the sample receptive surface of the membrane and may also be used to effect a lateral transport of the sample from one portion of the membrane to another.

2. Additional Dry Chemistry Reagent System

The above discussion, with respect to glucose analysis of whole blood, can by analog be readily extrapolated to the preparation of test strips and performance of clinical assays for a variety of other analytes typically found in biological fluid samples. The conditioned membrane system of this invention is, thus, applicable to clinical analysis of cholesterol, triglycerides, bilirubin, creatinine, urea and alpha-amylase. The assay format can be essentially the same as that described previously for glucose, or optionally involve the combination of the conditioned membrane/reagent system with one or more additional lamina (i.e. spreading layer, radiation blocking layer, semipermeable diffusion layer, etc.).

The preparation of a conditioned membrane, incorporating a dry chemistry reagent system for each of the above analytes, follows essentially the same process as described for preparation of glucose specific dry chemistry reagent systems (e.g. conditioning the membrane with a flow control agent and the absorption of the indicator/reagent cocktail). The conditioning of the membrane can, thus, occur prior to or concurrent with contact of the membrane with one or more of the constituents of the dry chemistry reagent systems.

A test strip for urea can be prepared by absorption, into a conditioned membrane, of appropriate concentrations of urease, buffer, and an indicator sensitive to changes in pH. When a whole blood sample is brought in contact with the sample receptive surface of the membrane, the serum is taken up by the membrane. The urea present in the serum is digested by the urease enzyme, thereby liberating ammonia in solution. The ammonia can then react with a suitable indicator (i.e., a protonated merocyanine dye). The pH of the membrane is buffered to about 8.0 to keep the equilibrium concentration of the ammonia relatively low. The indicator is monitored at 520 nm. Additional details of this specific reagent system are described in the open literature, see for example Spayd, R. W. et al., Clin. Chem., Vol. 24, No. 8 (1978) 1343.

A test strip for alpha-amylase can be prepared by absorption, into a conditioned membrane, of appropriate concentrations of a derivatized substrate (i.e., starch) and buffer. When the whole blood sample is applied to the sample receptive surface of the test strip, the serum is absorbed into the membrane, thus, initiating digestion of the derivatized substrate by the alpha-amylase in the sample. This digestion of the substrate releases a chromophore or fluorophore which can be monitored in accordance with accepted techniques and readily available equipment. Additional details for this specific reagent system also appear in the Spayd publication, previously referenced herein.

A test strip for bilirubin can be prepared by absorption, into a conditioned membrane, of appropriate concentrations of certain cationic polymers (i.e., polymeric quaternary salts) and phosphate buffer (pH approximately 7.4). When a whole blood sample is applied to the sample receptive surface of the test strip, the serum is absorbed into the membrane, thereby initiating interaction of the bilirubin and the cationic polymer. Such interaction results in a shift in the maximum absorption of the bilirubin from 440 to 460 nm with an accompanying substantial increase in absorption at the new peak. Additional details relating to this specific reagent system also appear in the previously referenced Spayd publication.

A test strip for triglycerides (triaclyglycerols) can be prepared by absorption, into a conditioned membrane, of surfactant, lipase, adenosine triphosphate (ATP), glycerol kinase and L-alph-glycerol phosphate oxidase, and a triarylimidazole leuco dye. In brief, the surfactant aids in dissociation of the lipoprotein complex so that the lipase can react with the triglycerides for form glycerol and fatty acids. The glycerol is then phospheroylated with the adenosine triphosphate in the presence of the glycerol kinase enzyme. The L-alpha-glycerol phosphate thus produced is then oxidized by the L-alpha-glycerol phosphate oxidase to dihydroxy acetone phosphate and hydrogen peroxide. The hydrogen peroxide oxidizes the leuco dye, producing a colored indicator which has a peak absorption at 640 nm. Additional details relating to this specific reagent system appear in the previously referenced Spayd publication.

An alternative and preferred chemistry reagent system for triglyceride analysis can be prepared by absorption, into a conditioned membrane, of lipase, glycerol dehydrogenase, p-iodonitrotetrozolium violet (INT) and diaphorase. The serum triglycerides initially interact with the chemistry reagent system and are hydrolyzed to free glycerol and fatty acids. The free glycerol is now converted to the dihydroxyacetone by glycerol dihydrogenase, in the presence of NAD. Simultaneous with such conversion, INT (colorless) is reduced by diaphorase, in the presence of NADH, to red dye (maximum, gamma=500 nm). The change in absorbence of the test strip at 500 nm is directly proportional to the concentration of serum triglycerides.

A test strip for determination of total cholersterol in serum can be prepared by absorption, into a conditioned membrane, of cholesterol ester hydrolase, cholesterol oxidase, a leuco dye and peroxidase. Upon application of a whole blood sample to the sample receptive surface of the test strip, the serum is absorbed into the membrane, thereby initiating conversion of the cholesterol esters to cholesterol, the oxidation of the cholesterol is accomplished by the cholesterol oxidase enzyme, thereby liberating peroxide. The peroxide and leuco dye then interact in the presence of peroxidase to form a highly colored indicator which can be monitored either visually or through the use of instrumentation. Additional details relating to this specific reagent system appear in the open literature, see Dappen, G. N., et al., Clin. Chem., Vol. 28, No. 5 (1982), 1159.

A test strip for creatinine can be prepared by absorption into a conditioned membrane of appropriate concentrations of creatinine iminohydrolase and an ammonia indicator (i.e., bromphenol blue). Upon application of a whole blood sample to the sample receptive surface of the test strip, the serum is absorbed into the membrane, thereby initiating interaction of the creatinine and the enzyme, creatinine amino hydrolase, resulting in the liberation of ammonia. The ammonia thereupon reacts with the indicator and the color development monitored visually or with conventional instrumentation. Additional details relating to this specific reagent appear in the open literature, see for example Toffaletti, J., et al., Clin. Chem., Vol. 29, No. 4 (1983), 684. It is also contemplated that the dry chemistry reagent systems of this invention be utilized in a multiple lamina test slide of the type developed by Eastman Kodak Company of Rochester, N.Y. (hereinafter "Kodak format"). Where a permeable material (i.e. spreading layer) is placed in contiguous contact with the sample receptive surface of a treated membrane, such contact will influence (change) the rate and quantity of whole blood/fluid transported through the membrane, and consequently the rate and extend of the reaction mediated by the analyte specific components within the membrane. At higher blood analyte levels, the transport of sample across the membrane can result in an overabundance of analyte and thus a foreshortening of the usable range of measurement.

FIG. 7 illustrates the adaptation of the test strip of this invention to a displacement immunoassay of the type described in Liotta U.S. Pat. No. 4,446,232, which is hereby incorporated by reference in its entirety. In the device exemplified in FIG. 7, the sample receptive surface of the membrane is coated with an enzyme labeled antigen or antibody (hereinafter "enzyme labeled conjugate"). The method of application of the coating to the sample receptive surface insures against penetration of the coating material into the matrix of the membrane. The balance of the immunochemistry reagent system, notably, a chromogenic or fluorogenic substrate for the enzyme, is incorporated into the conditioned membrane, so as to preserve its physical isolation from the surface coating. The contact of the sample with the coating on the surface of the membrane, results in displacement of enzyme labeled material. The displacement of the enzyme labeled conjugate is based upon the dynamic equilibrium which is caused by the presence of an analyte in the sample and the competition with the conjugate for binding to an analyte mimic in the surface coating.

The displaced enzyme labeled conjugate, along with a portion of the fluid fraction of the sample, is absorbed in the matrix of the membrane. The enzyme portion of this conjugate interacts with a substrate specific for the enzyme and thereby produces a discernible change in color or fluorescence which is indicative of the analyte of interest. This change can be observed visually, (in the case of color change) or by instrumentation designed for that purpose.

FIG. 8(b) depicts a novel membrane/wick composite having unique operational advantages. The wick's function in the composite are two-fold: (a) as an aid to the distribution of sample over the sample receptive surface of the membrane in the area defined by the aperture in the wick; and, (b) the absorption of excess sample, thereby modulating the amount of fluid which is absorbed by the membrane and preventing such excess from inadvertent transfer to other surfaces (notably the optical surfaces within a monitoring instrument of the type illustrated in FIG. 9). This limitation of the amount of sample which is absorbed by the membrane, produces a finite end point reaction which can be easily monitored.

The presence of the spreading layer may also be desirable where it is used to laterally transport the whole blood sample from its point of application on the test strip, to the situs of reaction, or where it contains reagents to pretreat or condition the sample prior to its absorption into the membrane. If a contiguous layer is used in conjunction with the membrane, the flow through the membrane may be modulated by changing the concentration of the flow control components contained in the impregnating vehicle (i.e. polyvinyl pyrolidone, polyethylene glycol, etc.). With an increase in the concentration of these components, the flow rate across the membrane is reduced and the usable range of measurement of the test strip preserved, thus, compensating for the presence of a contiguous wicking layer.

EXAMPLES

The Examples which follow further define, describe and illustrate some of the preferred embodiments of the method of preparation, use and evaluation of this dry reagent delivery systems of this invention. The equipment and techniques utilized in the preparation, use and evaluation of these dry reagent delivery systems are standard or as hereinbefore described. Parts and percentages appearing in such Examples are by weight unless otherwise stipulated.

EXAMPLE 1

A dry reagent delivery system is prepared, in accordance with the process of this invention, from the following materials and reagents:
(a) Membrane
  Millipore MF (mixed cellulose acetate-nitrate, and cellulose acetate
  density 4.9–6.5 mg/cm2
  porosity 0.01–0.45 (sample receptive surface)
(The porosity value is indicative of the differences in pore size from the more dense surface to less dense surface)
(b) Indicator ~1% (w/v) aqueous solution
  deionized water
  o-tolidine hydrochloride
(c) Glucose Specific Reagent Cocktail
  glucose oxidase 48 IU of activity/ml
  peroxidase 45 IU of activity/ml
  0.1 M citrate buffer
  stabilizer for enzyme—albumin 0.2% (w/v)
  conditioning and flow control agent—polyvinyl pyrolidone 3% (w/v)

The membrane is commercially available in rolls of one foot in width. For ease of handling, the membrane can be cut into strips or squares. Each of the above solutions are prepared fresh from reagent grade chemicals and deionized water. The membrane is initially contacted with the indicator solution by simply immersing the membrane in a trough containing this solution. The membrane is saturated with the indicator solution within 30 seconds, thereafter removed from the solution, drained and dried at room temperature or with mild heat.

After absorption of the indicator has been completed, this membrane is then contacted, exclusively from the relatively porous surface, with a solution containing the conditioning agent, flow control agent and glucose specific reagent cocktail. The take-up of this solution by the membrane is effected by simply floating membrane on the solution in a shallow tray and contacting the relatively porous (less dense) surface of the membrane with the surface of this solution much like one would blot up a spill with a sponge. Absorption of this solution by the membrane is fairly rapid, generally less than 30 seconds. The membrane is then air dried, residual moisture removed by vacuum drying (lyophilized) and stored to protect it from degradative influence light, oxygen, and moisture.

EXAMPLE 2

The procedures of Example 1 are repeated except for reversal of the order of contact of the indicator solution and the solution containing the conditioning reagent, flow control agent, and glucose specific reagent cocktail with this membrane.

EXAMPLE 3

The procedures of Example 1 are repeated except that the membrane is initially treated with a solution containing the conditioning agent. As noted previously in the test of this disclosure, the purpose of such treatment is to modify the internal structure of the membrane, to transform an essentially passive membrane to one which actively transports solute. The conditioning of the membrane also decreases its porosity, and increases the impedance to fluid flow throughout. Accordingly, the porosity gradient across the membrane is essentially eliminated thereby allowing either surface of the membrane to function as a sample receptive surface for a heterogenous fluid sample. The indicator solution and solution containing the flow control agent and the glucose specific reagent cocktail are thereafter sequentially imbibed onto the membrane in the manner described in Example 1.

EXAMPLE 4

A series of test strips, of the configuration of FIG. 2, are prepared incorporating the dry chemistry reagent systems of Examples 1, 2, and 3 respectively. Each category of test strips was then evaluated for rate of sample up-take, sensitivity, uniformity of indicator development and ease of use. The evaluation simply involved the transfer of a drop or two of fresh whole blood to the sample receptive surface of the membrane. Test strip performance was then determined by the monitoring of the observation side of the membrane for indicator development.

Both of the test strips of Examples 1 and 3 produced results which correlated well with one another over the range of 50 to 600 mg/dl. The test strip of Example 2 did not produce clinically reliable results. This lack of precision for the test strip of Example 2 was attributed to the inactivation of one or more of the enzymes of the reagent cocktail by the acidic indicator solution. It is, therefore, understood that the sequence of absorption of the various components of the reagnet cocktail into the membrane can be dictated by the relative compatibility of the pH of the carrier fluid. Where no such incompatibility is present, the order of absorption is not critical; and in fact will generally permit absorption of all of such components from a common (single) solution.

EXAMPLE 5

The following immunoassays adapt the conditioned membrane technology of this invention to some of the immunoassays which have traditionally been performed in solution or in the classis heterogenous format or in a multi-laminate solid phase format.

1. A test strip is prepared by initially coating a thin film containing a quantitative amount of peroxidase labeled betahuman chorionic gonadotropin hormone (beta-HCG conjugate) onto the sample receptive surface of a membrane of the same type used in Example 1. The beta-HCG conjugate is effectively immobilized in this coating by immunochemical binding of the antibody portion of the conjugate to a hapten mimic which is also present in the coating. Precautions are taken to insure that the conjugate is not also absorbed into the membrane matrix. Following such surface coating, the balance of this reagent system is absorbed into the membrane by absorption from the relative porous side. The sequence of absorption follows the experience gained in the preceding examples, namely, the indicator, o-tolidine (in an acidified vehicle), is absorbed first, followed by a second solution containing glucose oxidase, citrate buffer glucose and conditioning agent. The format of the test strip incorporating the dry chemistry reagent system, (which is specific for beta HCG), is the same as that described for FIG. 4.

A freshly voided sample of urine from a pregnant woman is collected in the early morning. This sample is then applied to the sample receptive surface of the test strip by simply dipping the test strip into the urine specimen. The beta-HCG in the urine specimen is thus brought into contact with the coating on the sample receptor surface of the test strip and a portion of the beta-HCG enzyme conjugate is displaced and binds to the analyte. This displacement of the conjugate by the analyte allows the conjugate to be absorbed into the test strip, where the enzyme portion thereof reacts with its corresponding substrate ($H_2O_2$), ultimately resulting in oxidation of the o-tolidine (and its conversion to a colored indicator). The development of color is, thus, indicative of the presence of analyte in the sample.

2. A test strip suitable for use in a competitive enzyme immunoassay is prepared by initial absorption of a substrate/color forming composition of Example 5(1) into the conditioned membrane. Also absorbed into the membrane is an enzyme (peroxidase) labelled antigen (i.e. beta-HCG). A specific quantitative amount of human beta-HCG antibody is coated onto the sample receptive surface of the membrane. A urine sample is then applied to the sample receptive surface of the membrane and the beta-HCG antibody on the surface reacts with the analyte in the sample. The immunochemical interaction of the analyte with the beta-HCG antibody impedes the absorption of the antibody into the matrix of the membrane. The relative concentration of analyte , thus, modulates the intensity of development of the indicator; the higher the concentration, the less intense color development. The extent of color development can be monitored visually or through the use of instrumentation.

Alternative indicator systems include fluorescent label conjugates (FIA) or radioisotope labelled conjugates (RIA). In each of these alternate assay formats, indicator concentrations would be monitored with instrumentation.

3. The sol particle immunoassay of Leuvering (U.S. Pat. No. 4,313,734—which is hereby incorporated by reference in its entirety) is adapted to the conditioned membrane assay format of this invention by simply imbibing beta-HCG labelled colloidal gold particles into the membrane. This reagent is applied to the membrane in quantitative amounts and dried, thereby imparting a uniform color to the membrane surface. An aliquot of sample (i.e. urine) is then applied to the sample receptive surface of the membrane. The presence of antigen in the sample is manifest by an aggregation of the beta-HCG labelled colloidal gold particles, thus, producing a discernible change in color which can be observed visually.

The foregoing Descripton and Examples have been provided as illustrative of a representative number of the preferred embodiments of this invention. It is not the intent of such Description and Examples to delineate the scope of this invention, which has been reserved to the claims that are set forth hereinafter.

What is claimed is:

1. A method for the preparation of a dry chemistry reagent system for analysis of heterogenous fluid samples, said method comprising:
 (a) providing a porous membrane having an essentially uniform composition, said porous membrane being characterized as having two planar surfaces and a porosity gradient from one planar surface to the other, the inherent porosity on at least one of said planar surfaces being essentially exclusive of particulate matter on the order of magnitude of cells present in biological fluid samples;
 (b) sequentially imbibing into said porous membrane (i) an indicator and (ii) a reagent cocktail specific for reaction with an analyte believed to be present in the fluid sample; and
 (c) contacting said porous membrane with an absorption effective amount of conditioning agent, said conditioning agent enhancing the absorption characteristics of the porous membrane to fluid samples, said contact of said porous membrane with a conditioning agent occurring either independent of and prior to time to contact of said porous membrane with an indicator or subsequent to contact of said porous membrane with said indicator.

2. The method of claim 1, wherein the porous membrane is conditioned with an absorption effective amount of a conditioning agent selected from the group consisting of albumin, polyvinyl pyrolidone, polyethylene glycol, carbohydrates, carboxymethyl cellulose (water soluble), methyl cellulose, glycerine and polyoxyethylene ethers.

3. The method of claim 1, wherein the porous membrane is cast from a material selected from the group consisting of a cellulose acetate-cellulose nitrate ester, nylon and polysulfone.

4. The method of claim 1, wherein the reagent cocktail is specific for glucose.

5. The method of claim 1, wherein the reagent cocktail is specific for cholesterol.

6. The method of claim 1, wherein the reagent cocktail is specific for urea.

7. The method of claim 1, wherein the reagent cocktail is specific for detection of an antigen or an antibody.

8. The method of claim 7, wherein the reagent cocktail contains an angiten or antibody which is conjugated to a mimic of an analyte.

9. The method of claim 7, wherein the reagent cocktail is specific for detection of hormones, pharmaceutical compounds, drugs of abuse or proteinaceous materials which are capable of evoking an immune response.

10. The method of claim 7, wherein a portion of the reagent cocktail is deposited upon one of the planar surfaces of the porous membrane so as to be retained thereon without substantial penetration into the matrix of the porous membrane.

11. A dry chemistry reagent system for detection of an analyte in a heterogenous fluid sample, said system comprising:
 a porous membrane of essentially uniform composition and a porosity gradient from one planar surface thereof to the other, wherein said porous membrane's inherent fluid absorption and distribution characteristics have been modified by imbibing a conditioning agent, an indicator, flow control agent and reagent cocktail into its matrix, the effect of such absorption being to effect an essentially uniform distribution of indicator, flow control agent and reagent cocktail within the porous membrane thereby enhancing the uniformity of internal structure of said film so as to enhance the uniformity of absorption and modulate the rate of absorption of the fluid sample and its interaction with the reagent cocktail.

12. The system of claim 11, wherein the porous membrane is conditioned with an absorption effective amount of a conditioning agent selected from the group consisting of albumin, polyvinyl pyrolidone, polyethylene glycol, carbohydrates, carboxymethyl cellulose, methyl cellulose, glycerine and polyoxyethylene ethers.

13. The system of claim 11, wherein the porous membrane is cast from a material selected from the group consisting of a cellulose acetatecellulose nitrate ester, nylon and polysulfone.

14. The system of claim 11, wherein the reagent cocktail is specific for detection of glucose.

15. The system of claim 11, wherein the reagent cocktail is specific for detection of cholesterol.

16. The system of claim 11, wherein the reagent cocktail is specific for detection of urea.

17. The system of claim 11, wherein the reagent cocktail is specific for detection of an antigen or an antibody.

18. The system of claim 17, wherein the reagent cocktail contains an antigen or antibody which is conjugated to a mimic of an analyte.

19. The system of claim 17, wherein the reagent cocktail is specific for detection of hormones, pharmaceutical compounds, drugs of abuse or proteinaceous materials which are capable of evoking an immune response.

20. The system of claim 17, wherein a portion of the reagent cocktail is deposited upon one of the planar surfaces of the porous membrane so as to be retained thereon without substantial penetration into the matrix of the porous membrane.

21. A rapid analytical method for screening a heterogenous fluid sample for an analyte of interest, comprising:
(a) providing a dry chemistry reagent system comprising a porous membrane of essentially uniform composition and a porosity gradient from one planar surface thereof to the other, wherein said porouse membrane's inherent fluid absorption characteristics have been modified by sequentially imbibing a conditioning agent, an indicator, flow control agent and reagent cocktail into its matrix, the effect of such absorption being to effect an essentially uniform distribution of indicator, flow control agent and reagent cocktail within the porous membrane thereby enhancing the uniformity of internal structure of said porous membrane so as to modulate both the rate and the uniformity of absorption of the fluid sample and its interaction with the reagent cocktail;
(b) applying a heterogenous fluid sample to the sample receptive surface of the bibulous medium of the reagent system; and
(c) monitoring the surface of the bibulous medium opposite to the sample receptive surface for a change of color or fluorescence or for the development of color or fluorescence.

22. The analytical method of claim 21, wherein the porous membrane is conditioned with an absorption effective amount of a conditioning agent selected from the group consisting of albumin, polyvinyl pyrolidone, polyethylene glycol, carbohydrates, carboxymethyl cellulose, methyl cellulose, glycerine and polyoxyethylene ethers.

23. The analytical method of claim 21, wherein the porous membrane is cast from a material selected from the group consisting of a cellulose acetate-cellulose nitrate ester, nylon and polysulfone.

24. The analytical method of claim 21, wherein the reagent cocktail is specific for detection of glucose.

25. The analytical method of claim 21, wherein the reagent cocktail is specific for detection of cholesterol.

26. The analytical method of claim 21, wherein the reagent cocktail is specific for detection of urea.

27. The analytical method of claim 21, wherein the reagent cocktail is specific for detection of an antigen or an antibody.

28. The analytical method of claim 27, wherein the reagent cocktail contains an antigen or antibody which is conjugated to a mimic of an analyte.

29. The analytical method of claim 27, wherein the reagent cocktail is specific for detection of hormones, pharmaceutical compounds, drugs of abuse or proteinaceous materials which are capable of evoking an immune response.

30. The analytical method of claim 27, wherein a portion of the reagent cocktail is deposited upon one of the planar surfaces of the porous membrane so as to be retained thereon without substantial penetration into the matrix of the porous membrane.

31. A test kit for analysis of a heterogenous fluid sample, said kit comprising:
(a) dry chemistry reagent system comprising a porous membrane of essentially uniform composition and a porosity gradient from one planar surface thereof to the other, wherein said porous membrane inherent fluid absorption and distribution characteristics have been modified by sequentially imbibing a conditioning agent, an indicator and reagent cocktail into its matrix, the effect of such absorption being to effect an essentially uniform distribution of indicator, flow control agent and reagent cocktail within the porous membrane thereby enhancing the uniformity of internal structure of said film so as to modulate both the rate and uniformity of absorption of the fluid sample and its interaction with the reagent cocktail; and
(b) a standard for comparison with the indicator of the dry chemistry reagent system.

32. The test kit of claim 31, wherein the porous membrane is conditioned with an absorption effective amount of a conditioning agent selected from the group consisting of albumin, polyvinyl pyrolidone, polyethylene glycol, carbohydrates, carboxymethyl cellulose, methyl cellulose, glycerine and polyoxyethylene ethers.

33. The test kit of claim 31, wherein the porous membrane is cast from a material selected form the group consisting of a cellulose acetatecellulose nitrate ester, nylon and polysulfone.

34. The test kit of claim 31, wherein the reagent cocktail is specific for detection of glucose.

35. The test kit of claim 31, wherein the reagent cocktail is specific for detection of cholesterol.

36. The test kit of claim 31, wherein the reagent cocktail is specific for detection of urea.

37. The test kit of claim 31, wherein the reagent cocktail is specific for detection of an antigen or an antibody.

38. The test kit of claim 37, wherein the reagent cocktail contains an antigen or antibody which is conjugated to a mimic of an analyte.

39. The test kit of claim 37, wherein the reagent cocktail is specific for detection of hormones, pharmaceutical compounds, drugs of abuse or proteinaceous materials which are capable of evoking an immune response.

40. The test kit of claim 37, wherein a portion of the reagent cocktail is deposited upon one of the planar surfaces of the porous membrane so as to be retained thereon without substantial penetration into the matrix of the bibulous film.

* * * * *